US012705774B2

(12) United States Patent
Cedilnik et al.

(10) Patent No.: US 12,705,774 B2
(45) Date of Patent: Aug. 11, 2026

(54) METHOD FOR THE EVALUATION OF THE THICKNESS OF A TISSUE OF AN ORGAN

(71) Applicant: INHEART, Pessac (FR)

(72) Inventors: Nicolas Cedilnik, Pessac (FR); Jean-Marc Peyrat, Pessac (FR)

(73) Assignee: INHEART, Pessac (FR)

( * ) Notice: Subject to any disclaimer, the term of this patent is extended or adjusted under 35 U.S.C. 154(b) by 216 days.

(21) Appl. No.: 18/242,636

(22) Filed: Sep. 6, 2023

(65) Prior Publication Data

US 2024/0087153 A1 Mar. 14, 2024

(30) Foreign Application Priority Data

Sep. 7, 2022 (EP) .................................... 22194410

(51) Int. Cl.
*G06T 7/60* (2017.01)
*A61B 34/10* (2016.01)
(Continued)

(52) U.S. Cl.
CPC ................ *G06T 7/60* (2013.01); *A61B 34/10* (2016.02); *G06T 7/0012* (2013.01); *G06T 7/12* (2017.01); *G06T 17/20* (2013.01); *G06T 19/20* (2013.01); *G16H 50/50* (2018.01); *A61B 2034/105* (2016.02); *G06T 2207/10028* (2013.01);
(Continued)

(58) Field of Classification Search
CPC ............................... G06T 7/0012; G06T 7/60
See application file for complete search history.

(56) References Cited

U.S. PATENT DOCUMENTS

2019/0355280 A1* 11/2019 Champ ................ B29C 64/393

OTHER PUBLICATIONS

Yezzi et al., "An Eulerian PDE approach for computing tissue thickness," in IEEE Transactions on Medical Imaging, vol. 22, No. 10, pp. 1332-1339, Oct. 2003 (Year: 2003).*

(Continued)

*Primary Examiner* — Matthew Salvucci
(74) *Attorney, Agent, or Firm* — Greer, Burns & Crain, Ltd.

(57) ABSTRACT

A computer-implemented method for the evaluation of an adjusted thickness of a tissue of an organ, the method comprising:

step (1) of receiving at least one mapping of points (10) representing said tissue, said mapping of points (10) defining an inner border (102) and an outer border (101) of said tissue;

step (2) of segmentation of the mapping of points (10) by classification of each point (11) from the mapping of points (10) into a class belonging to a set of different classes;

step (3) of determining a plurality of trajectories (109) each joining one point (108) of the inner border (102) to one point (107) of the outer border (101);

step (4) of computing for each trajectory (109) the value of a thickness function depends on said trajectory (109) and the classes assigned to the points of the mapping of points (10) through which said trajectory encompasses; and step (5) of generation of a 3D model (1000) of said tissue from said mapping of points (10), wherein at least to each voxel of said 3D model (1000) corresponding to the inner border (102) and/or to the outer border (101) of said tissue is assigned an adjusted thickness value determined from the value of the thickness function associated to the trajectory encompassing said voxels.

10 Claims, 4 Drawing Sheets

(51) Int. Cl.
*G06T 7/00* (2017.01)
*G06T 7/12* (2017.01)
*G06T 17/20* (2006.01)
*G06T 19/20* (2011.01)
*G16H 50/50* (2018.01)

(52) U.S. Cl.
CPC ............... *G06T 2207/30048* (2013.01); *G06T 2207/30241* (2013.01); *G06T 2210/41* (2013.01); *G06T 2210/56* (2013.01); *G06T 2219/2012* (2013.01)

(56) References Cited

OTHER PUBLICATIONS

O'Donnell, T., et al., "Comprehensive Cardiovascular Image Analysis Using MR and CT at Siemens Corporate Research", International Journal of Computer Vision, Nov. 1, 2006, pp. 165-178, vol. 70, No. 2.

Xiong, G., et al., "Comprehensive Modeling and Visualization of Cardiac Anatomy and Physiology from CT Imaging and Computer Simulations", IEEE Transactions On Visualization and Computer Graphics, Feb. 1, 2017, pp. 1014-1028, vol. 23, No. 2.

Yezzi, A., et al., "A PDE Approach for Measuring Tissue Thickness", Proceed:INGS 2001 :IEEE Conference On Computer VJ:SJ:On and Pattern Recognj:TJ:On. CVPR 2001, Dec. 8, 2001, pp. 1-87-1-92, vol. 1, No. 8.

European Search Report dated Feb. 24, 2023 for European Application No. EP 22 19 4410.

* cited by examiner

[Figure 1]
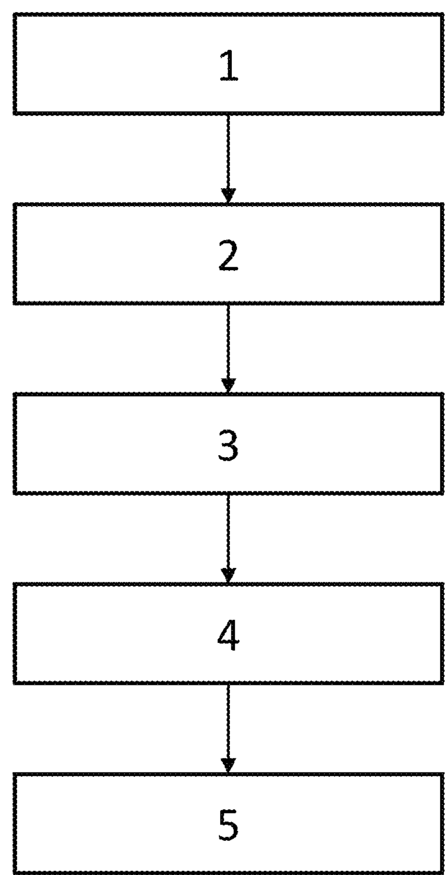
[Figure 2]
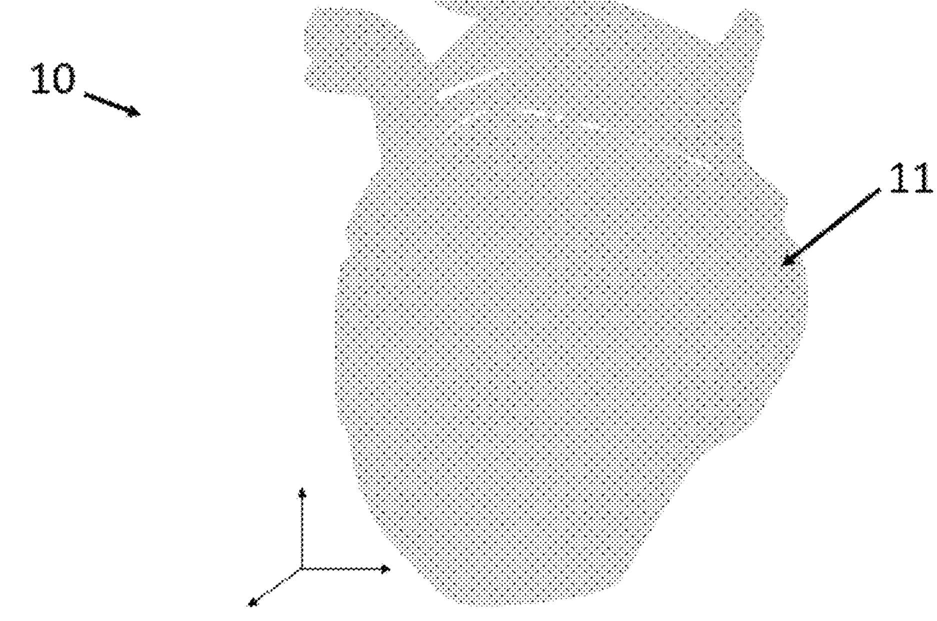

[Figure 3]
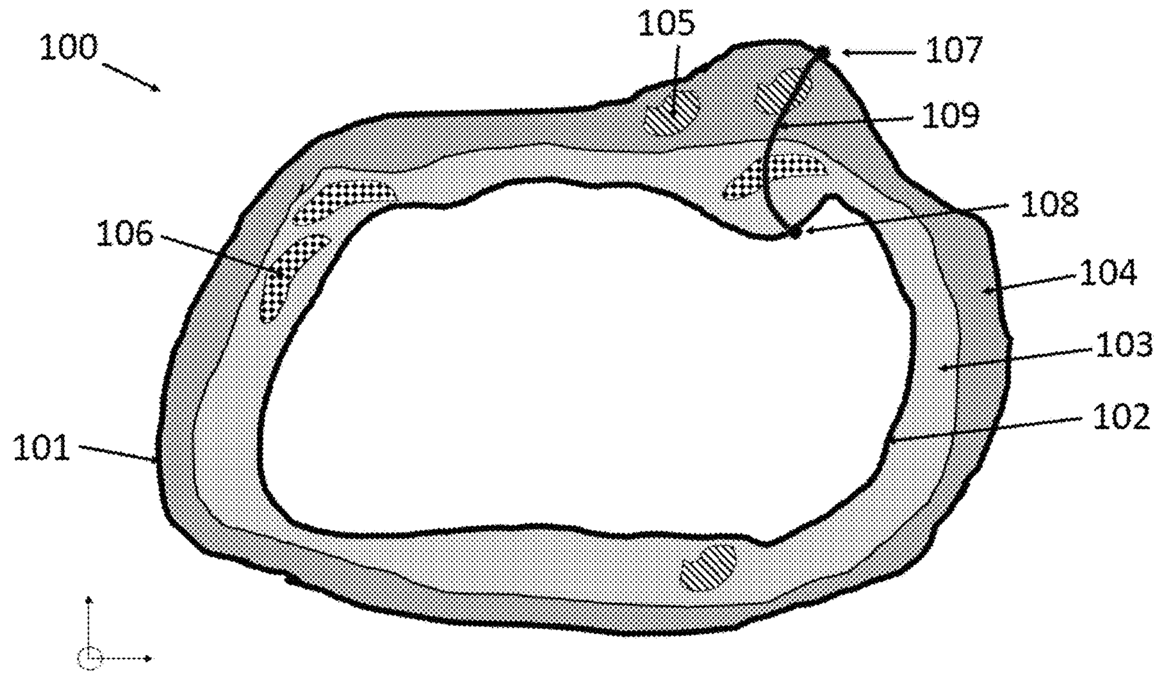
[Figure 4A]
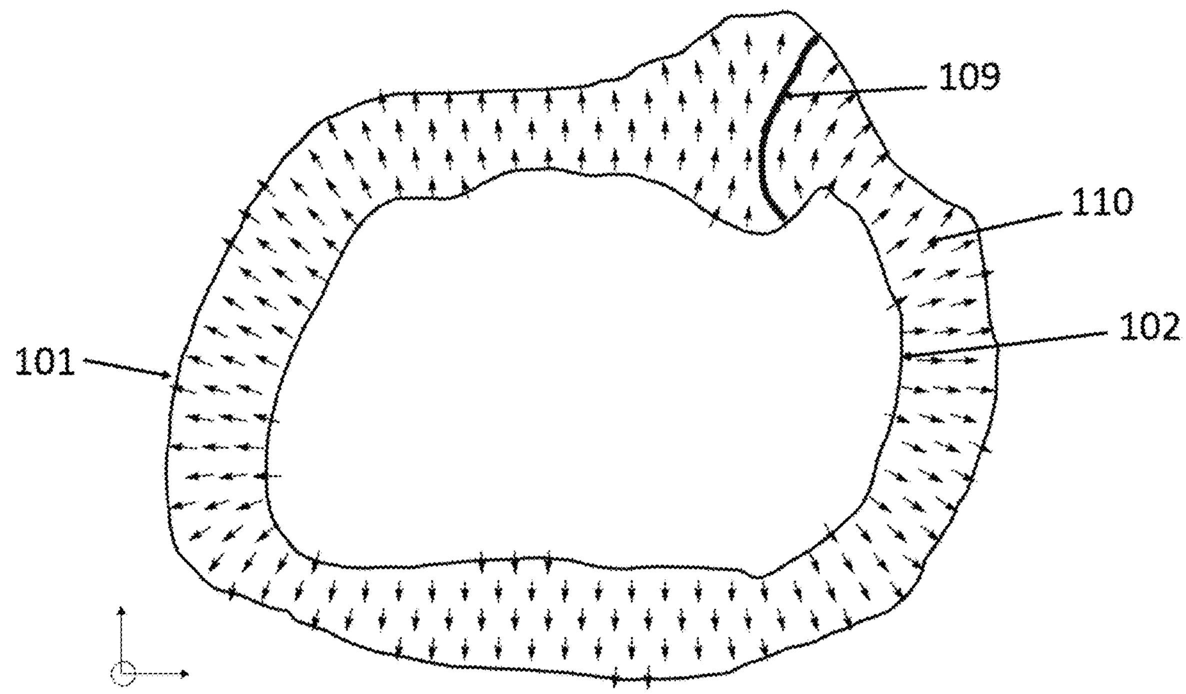

[Figure 4B]
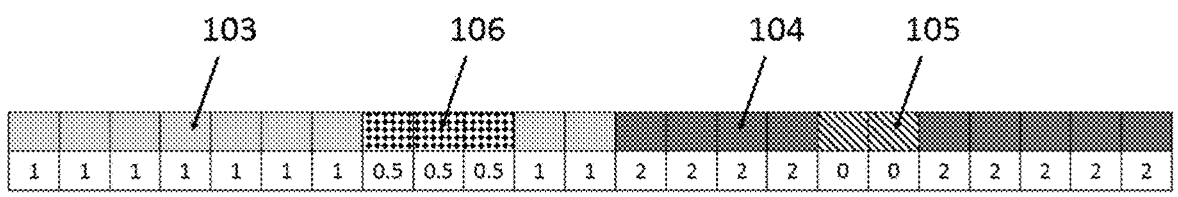
[Figure 4C]
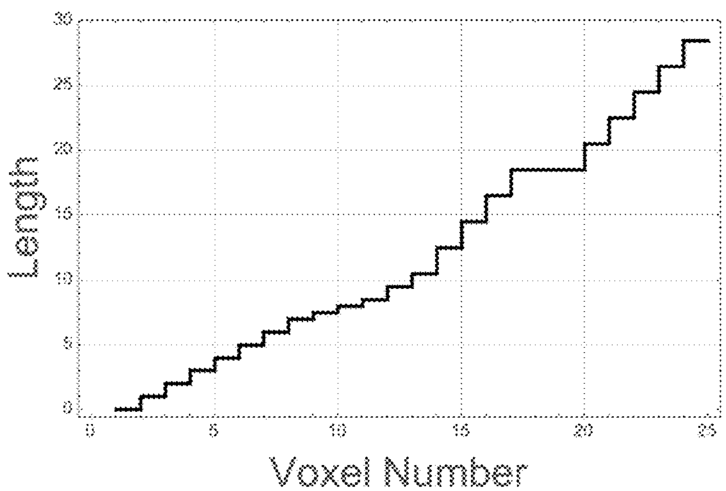

[Figure 5]
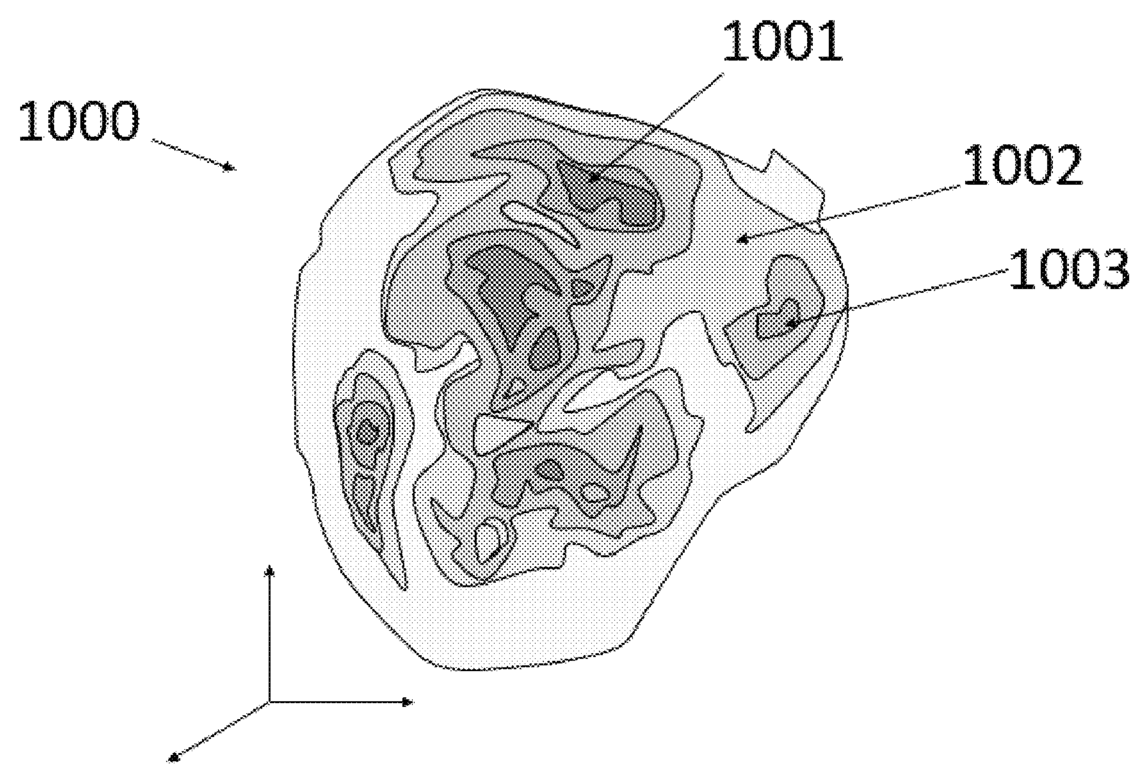

METHOD FOR THE EVALUATION OF THE THICKNESS OF A TISSUE OF AN ORGAN

CROSS-REFERENCE TO RELATED APPLICATIONS

This application claims the benefit of foreign priority to European patent application EP 22194410.1 filed Sep. 7, 2022, the entire disclosure of which is herein incorporated by reference.

TECHNICAL FIELD

The present invention relates to the field of computer assisted medical diagnosis. More particularly, the invention relates to a method for the computational evaluation of the thickness of a wall of an organ of a patient.

BACKGROUND

Many diseases affecting an organ in the body, such as hepatitis or encephalitis, result in a change in the morphology of said organ, notably its shape and its size. In such case, the measure of the thickness of some tissues of the organ can be used to infer an estimation of the health of the organ and of the patient. Some diseases such as hypertrophic cardiomyopathy and myocardial infarction have an impact on the thickness of the wall of the heart, aneurysm also modify the thickness of the vein or artery where said aneurysm is located.

Evaluation of the thickness of a tissue of an organ is generally done with measuring the distance separating closest points of inner and outer surface of the tissue. Nevertheless, some diseases may modify the cellular composition of some organs. For example, in the case of some cardiac diseases, part of the muscular tissue is replaced by adipocytes or by calcified structures; such structural changes tend to weaken the thickness of the heart well.

Furthermore, since the cellular composition of an organ is, in general, heterogeneous, the diversity of elements forming such cellular composition needs to be considered to accurately estimate the thickness of said tissue of an organ in such a way that the estimated thickness value is correct. Finally, a tissue may be composed by several cell layers with different histological characteristics; in such a case, the estimation of a thickness value needs to consider this histological diversity to return a result of higher medical relevance.

Considering the above, there is therefore a need for a method for computer assisted estimation of the thickness of a tissue of an organ capable of inferring the thickness value even when said tissue is composed of heterogeneous types of cells.

SUMMARY

The object of the present invention is to answer to this need.

For this purpose, the subject of the invention is a computer-implemented method for the evaluation of an adjusted thickness of a tissue of an organ, the method comprising:

- step (1) of receiving at least one mapping of points representing said tissue, said mapping of points defining an inner border and an outer border of said tissue;
- step (2) of segmentation of the mapping of points by classification of each point from the mapping of points into a class belonging to a set of different classes;
- step (3) of determining a plurality of trajectories each joining one point of the inner border (IB) to one point of the outer border;
- step (4) of computing for each trajectory the value of a thickness function, said thickness function depends on said trajectory and the classes assigned to the points of the mapping of points through which said trajectory encompasses;
- step (5) of generation of a 3D model of said tissue from said mapping of points, at least to one voxel of said 3D model is assigned an adjusted thickness value determined from the value of the thickness function associated to the trajectory encompassing said voxels.

According to the invention, the mapping of points representing a tissue of an organ comprises two spatial subregions named "inner border" and an "outer border". Each of the borders are defined by subsets of points from the mapping of points. Both inner and outer borders are required to delimitate the space for which an adjusted thickness value will be computed in a subsequent step, said adjusted thickness value depending on a distance between the two borders. The distance formula may be defined in terms of discrete or continuous arguments, such as the number of voxels satisfying some constraint as belong to a specific sequence of voxels.

According to the invention, the step of segmentation of the mapping of points makes possible to differentiate the plurality of structures underlying the mapping of points. By associating a class to each point of the mapping of points, it is possible to identify stacked structures and take into account the spatial arrangement of said structures to improve the accuracy of the method. In general, said structures may correspond to elements of different histological nature such as calcified structures, fat cells or muscular cells. Additionally, muscular cells can be associated to different classes by considering different quality levels of said muscular cells, classes of muscular tissue can be discrete: "good quality", "medium quality", or "poor quality", or continuously indexed by a numerical parameter identifying a particular muscular tissue quality.

In the context of the present specification, unless expressly provided otherwise, a "trajectory of points" denotes an ordered sequence of points of a mapping of points or an ordered sequence of voxels of a set of voxels.

By determining a set of trajectories joining one point of the inner border to one point of the outer border, it is possible to define, in the direction of a given trajectory, an adjusted thickness value of the mapping of points based on the length of said trajectory.

By determining the thickness function value of every trajectory, it is possible to construct a 3D model representing the adjusted thickness along every trajectory and therefore the adjusted thickness of the global mapping of points. The method of the invention allows to consider for example the wall of the heart, better known as the myocardium. In this case, the 3D image or the 3D model of the heart can be segmented into different equivalence classes according to a thickness criterion, the 3D model representing therefore a thickness map of the heart.

In the context of the present specification, unless expressly provided otherwise, a "mapping of points" is a set of points, said points can be encoded computationally by sequences or lists of numerical values, in particular sequences of at least one numerical value representing the coordinates of said points in a particular reference. The coordinates can be specified in any type of chart, for instance in cartesian, spherical cylindrical coordinates or any other type of geometrical chart in one, two or three spatial dimensions. A mapping of points might be 2D mapping of points or a 3D mapping of points.

A 3D mapping of points might be a 3D model of the organ, namely one or more structured mesh, each comprising a plurality of vertices connected with each other to define a plurality of faces and/or volumes which approximate internal and/or external surfaces and/or volumes of all or part of the organ. A 3D model might be a triangle mesh or a quadrilateral mesh, or more generally a polygonal mesh, which comprises a plurality of vertices, with edges connecting pairs of vertices and/or polygonal faces connecting a closed set of vertices. As a variant, a 3D model might be a tetrahedral mesh or a hexahedral mesh or a prism mesh, or more generally a volume mesh, which comprises a plurality of vertices, with polyhedrons connecting a closed set of polygons defined by closed set of vertices. Preferably, each vertex and/or edge and/or polygon and/or polyhedron might be labelled as being a part of a specific sub-part of the organ. A 3D model might be stored as a list of vertices each associated with spatial coordinates and with a set of connections to other vertices, or as a list of vertices associated with spatial coordinates and a list of polygons or faces each defined by a subset of vertices contained in said list of vertices, being understood that any other suitable method of storage might be used in the context of the present specification.

A 3D mapping of points might be an unstructured set of points, namely a point cloud, where each point might be or not connected to another point of the point cloud.

In the context of the present specification, said “3D mapping of points” might be (or might be computed from) one of, or a combination of two or more of: an electrophysiological map, resulting from an electrocardiogram (ECG) and/or from invasive mapping, an anatomical and/or a functional map, resulting from as a computed tomography (CT)-scan, a positron emission tomography (PET)-scan, a single photon emission computed tomography (SPECT) scan or a magnetic resonance imaging (MRI)-scan, and an electro-anatomical map, resulting from an invasive mapping.

In the context of the present specification, unless expressly provided otherwise, a “computer” may refer, but is not limited to, a desktop computer, a laptop computer, a tablet computer, a piece of testing equipment, a network appliance, a controller, a digital signal processor, a computational engine within an appliance, a consumer-electronic device, a portable computing device, and/or another electronic device, and/or any combination thereof appropriate to the relevant task at hand. Moreover, the method steps might be all executed on a same device. As a variant, the method steps might be executed on several devices, connected by wires or by a wireless connection.

According to one embodiment, to each point of the mapping of points which is received is associated at least one value depending on the type of the tissue at a location corresponding to said point, and the step of segmentation is implemented by associating a class selected from the set of classes from said value associated to said point of the mapping of points.

In this way, each point of the mapping of points can be classified by associating, according to the at least one value, a class among the set of classes. In particular, a classification function receives a point and the associated at least one value then returns the associated class of the point. The at least one value may be a numerical value in terms of Hounsfield units, or a sequence of different numerical values encoding a physical property of said point.

The classification of each point of the mapping of points can be performed by comparing the at least one value associated to said point to a numerical threshold. Said comparison can be performed by first evaluating a mathematical function on the at least one value and comparing the result to said threshold. Alternatively, the classification of each point of the mapping of points can be performed by first applying some morphological transformation on the mapping of points, such as a filter, then a thresholding action of the transformed points, making possible to infer a class from a relative density of points.

Alternatively, or cumulatively, classification of points can be done by means of a region growing procedure, starting from a detected region of interest; the step of detecting a region of interest and classifying this region of interest can be performed, at least partially, manually by a user.

Advantageously, the segmentation classes comprise at least one class among muscle tissue, fat tissue or calcified tissue.

In this way, it is possible to estimate the adjusted thickness of a region of interest constituted by a mixture of muscle tissue, fat tissue and/or calcified tissue in such a way that the computation of the thickness of the muscular part of said region do not consider, or consider it only up to a penalization factor, the fat tissue and calcified tissue of said region. By proceeding this way, the resulting 3D model shows the adjusted thickness along every trajectory based on the effective muscular composition associated to the mapping of points.

According to one embodiment, the plurality of trajectories is defined from a vector field pointing from the inner border to the outer border. Preferably, said vector field might be a normalized vector field.

In this way, the vector field defines a partition of the mapping of points into a set of disjoints trajectories. Therefore, for each point of the mapping of points, there is a unique trajectory encompassing by said point and joining a unique point from the inner border to a unique point of the outer border.

According to an embodiment, said trajectories can be determined as the orbits of a given vector field, said vector field might be oriented from the inner border to the outer border or oriented from the outer border to the inner border.

Advantageously, said vector field may be defined as the gradient vector field of a scalar function U.

Advantageously, said vector field may be defined as the gradient vector field of a scalar function U, solution of the following Dirichlet problem:

$$A \in \mathbb{R}, B \in \mathbb{R}, A<B, \Delta U=0, U_{|InnerBorder}=A, U_{|OuterBorder}=B, \quad \text{[Math.1]}$$

In this way, it is possible to take advantage of the well-known fact that harmonic functions with this regularity satisfy a maximum principle as well as some monotonicity properties. Proceeding this way, one ensures that the solution U is a monotone function with maximum B attained everywhere in the outer border and minimum A attained everywhere in the inner border. Consequently, the gradient of said solution U, denoted by T, is a vector field pointing from the inner border to the outer border.

In this way, the trajectories are defined as the orbits of the vector field, that is, said trajectories are tangentially positioned with respect of the vector field. This characteristic makes possible to define, for a given orbit, the thickness function value of said orbit as a length of this orbit.

According to one embodiment, the thickness function value associated to a trajectory is computed from a value of the arclength of said trajectory. Advantageously, the computation of the arclength of said trajectory may use weighted with coefficients depending on classes assigned to the points of the mapping of points through which said trajectory encompasses.

Without restriction of generality, the arclength formula can be written such that it takes the form of:

$$L(O) = \int_{O} 1 dx \quad \text{[Math. 2]}$$

where the integration measure dx can be a continuous measure, such as the Lebesgue measure, or a finite measure such as the counting measure.

The arclength formula employed for the computation of the thickness function value may consider at least one penalization term which is a function of the different classes conforming the model, said function may be nonlinear. In such a case, the arclength formula writes:

$$L(O)=\int_{O} F(C_1, \ldots, C_n)dx, \quad \text{[Math.3]}$$

where F is a function of the classes C1 up to Cn, and the integrand corresponds to the penalization term.

According to one embodiment, the thickness function value associated to a trajectory is computed with instantiating said arclength function value to 0, with traversing a set of points of the mapping of points encompassed by said trajectory and with recursively computing a new value of said arclength value for each new traversed point, said new value being computed from the previous value of said thickness function value and from the class assigned to said new traversed point.

In this way, the arclength value of any trajectory is computed iteratively over the points forming said trajectory. By starting from the inner or the outer border, it is possible to update recursively the value of the arclength by adding the weighted contribution of consecutive voxels in the trajectory until there is a voxel belonging to the opposite border.

Since arclength is defined as a weighted sum over the voxels forming said trajectory. Weights appearing in the arclength computation represent penalty coefficients indicating for each voxel of said trajectory, the effective contribution to the arclength computation according to the class of said voxel.

According to one embodiment, said new value is computed from the previous value of said thickness function value incremented by a factor whose value depends on the class assigned to said new traversed point.

In this way, the computation ensures that each voxel contributes to the arclength computation accordingly to its class. Therefore, the total arclength that is returned correctly penalize regions that contribute in a different manner to the result. This is the case when fat tissue or calcified tissue is between two disjoint muscular parts of the tissue.

According to one embodiment, the factor value is a non-null step value when the class assigned to said new traversed point is a predetermined class and 0 otherwise.

In this way, the method ensures that only points belonging to said predetermined class will be taken into account in the computation of the arclength of a given trajectory. This is particularly important when, for example, only muscular tissue is measured, dropping out of the computation any other type of tissue.

According to one embodiment, said factor value depends on the number of points to which said predetermined class is assigned among a set of points included into a bounding region centered on said new traversed point.

In this way, it is possible to establish a ponderation of the arclength computation based on the global distribution of classes among the mapping of points. For example, in the case that a given class is the dominant class inside a bounding region, the factor of a given point will be a function of the percentage of the class of said point among the total number of points inside said bounding region.

According to one embodiment, to at least to each voxel of said 3D model corresponding to the inner border and/or to the outer border of said tissue is assigned an adjusted thickness value determined from the value of the thickness function associated to the trajectory encompassing said voxels.

According to one embodiment, to each voxel of said 3D model corresponding to the inner border and/or to the outer border of said tissue is assigned a color determined from the thickness value assigned to this voxel, said color being selected from a set of colors each associated to a thickness range.

In this way, it is possible to render the segmented 3D model in a way that each class is correctly represented for visualization purposes. In particular, the class encoding muscular tissue can be associated to a first color and in the case that a diversity of points associated to muscular tissue presenting different qualities, a gradient color scheme may be used to indicate the same histological class while it allows to represent a variability inside said class.

According to one embodiment, said generated 3D model of said tissue comprises a plurality of sub-meshes, and each sub-mesh is associated to a predetermined thickness range and comprises each voxel of said 3D model whose thickness value assigned to this voxel belongs to this predetermined thickness range.

In this way, each sub-mesh is defined as the set of points of the mapping of points that belong to the same trajectory. Since there is an adjusted thickness value associated to any given trajectory, any point of said predetermined thickness range must be corresponded with said adjusted thickness value.

The present invention will be better understood, and other advantages will appear, on reading the detailed description of an embodiment taken by way of non-limiting example and illustrated by the appended drawings.

BRIEF DESCRIPTION OF THE DRAWINGS

FIG. 1 is a logic flow diagram that depicts a computer-implemented method, according to an embodiment of the invention;

FIG. 2 shows a schematic representation of a 3D mapping of points representing a tissue of an organ;

FIG. 3 is a schematic view of a 2D slice of a tissue of an organ comprising different classes of sub-tissues;

FIG. 4A represents the computation of the arclength of a trajectory passing through different classes of sub-tissues;

FIG. 4B represents the evolution of the adjusted thickness value of a trajectory passing through different classes of sub-tissue at each step of the computation;

FIG. 4C represents a plot of the progression at each step of the computation of the thickness function value;

FIG. 5 represents a schematic view of a 3D model resulting from the method of FIG. 1.

DETAILED DESCRIPTION

The methods disclosed herein may also be implemented by software programs executable by a computer system. Further, implementations may include distributed processing and parallel processing, especially for processing in parallel several or all data in the data sets.

The illustrations described herein are intended to provide a general understanding of the structure of various embodiments. These illustrations are not intended to serve as a complete description of all the elements and features of apparatus, processors and systems that utilizes the structures or methods described therein. Many other embodiments or combinations thereof may be apparent to those of ordinary skills in the art upon reviewing the disclosure by combining the disclosed embodiments. Other embodiments may be utilized and derived from the disclosure, such that structural and logical substitutions and changes may be made without departing from the scope of the disclosure.

Further, the disclosure and the illustrations are to be considered as illustrative rather than restrictive, and the appended claims are intended to cover all such modifications, enhancements, and other embodiments, which fall within the true spirit and scope of the description. Thus, the scope of the following claims is to be determined by the broadest permissible interpretation of the claims and their equivalents and shall not be restricted or limited by the foregoing description.

Reference is made to FIG. 1 which shows a computer-implemented method for the evaluation of the adjusted thickness of a tissue of an organ.

In an initial step 1, at least one mapping of points 10 representing said tissue is received, said mapping of points 10 defining and inner border 102 and an outer border 101 of said tissue.

Reference is made to FIG. 2 which shows a 3D mapping of points of a tissue of a patient's heart, for instance acquired from a CT-scan method. Said tissue comprises an inner border 102 and an outer border 101, which corresponds to inner and outer border points of said 3D mapping of points.

The points of the mapping of points are computationally stored through the 3D coordinates of said points. Moreover, each point is associated to a numerical value in terms of Hounsfield units encoding the radiodensity at said point.

Such a mapping of points is received by the computer implemented method for the evaluation of the adjusted thickness of said tissue at step 1.

In a subsequent step 2 of segmentation of the mapping of points 10 by classification of each point 11 from the mapping of points 10 into a class belonging to a set of different classes.

Classification procedure starts by reading each numerical value associated to each point 11 of the mapping of points 10 and applying a function, advantageously a softmax function, to said numerical value and comparing the result of the computation to a threshold from a list of thresholds of cardinality equals to number of classes, the effective class associated to said point 11 will be the class for which said results overpasses said threshold.

Reference is made to FIG. 3 which shows a segmented 2D slice of the mapping of points of FIG. 2, resulting from said segmentation step. Said tissue is composed by several classes of tissues 103, 104, 105 and 106. In this embodiment, tissues 103 and 104 corresponds to muscular tissue with different quality levels, and tissues 105 and 106 corresponds to adipocytes and to calcified structures respectively.

In a subsequent step 3 of determining a plurality of trajectories each joining one point of the inner border 102 to one point of the outer border 101.

Step 3 comprises a first sub-step 3.1 of determining the solution U of the Laplace equation with homogenous Dirichlet boundary condition on the inner border 102 and inhomogeneous Dirichlet boundary condition, equals to 1, on the outer border 101.

Step 3 comprises a sub-step 3.2 of computation of the gradient vector field of the solution U obtained in step 3.1 and normalizing said gradient with respect to the Euclidean norm for finally returning the normalized vector field 10.

Step 3 comprises a sub-step 3.3 of computing the orbits of the said normalized gradient vector field 10 by integrating, for each point 18 of the inner boundary 102, a Cauchy problem where the dynamics of the ordinary differential equation is defined by said normalized gradient vector field 10 and the initial condition is given by the coordinates of said point 18.

In this embodiment, said vector field is the normalized gradient field of the unique solution the non-homogeneous Dirichlet problem [Math.1].

Reference is made to FIG. 4A showing a view of the 2D slice of FIG. 3 over which is defined a vector field resulting from step 3 and pointing from the inner border to the outer border, said vector field defines a plurality of trajectories.

Is also represented on FIG. 4A a trajectory 109 joining one point 108 of the inner border 102 to one point 107 of the outer border 101.

In a subsequent step 4 of computing for each trajectory 109 the value of a thickness function, said thickness function depends on said trajectory and the classes assigned to the points of the mapping of points through which said trajectory encompasses. In this embodiment, the thickness function value associated to said trajectory 109 is computed from a value of the arclength of said trajectory weighted with coefficients depending on classes assigned to the points through which said trajectory encompasses.

Reference is made to FIG. 4B which shows the computation of the arclength of a trajectory 109 joining one point 108 of the inner border 102 to one point 107 of the outer border 101 and passing through points that have been classified into different classes during classification step 2. To each class, it is associated a weight, said weight allows to quantify some physical property, such as density, solubility, or water content, of the tissue to which said class is related.

In this embodiment, four types of tissue are encoded into four classes 103, 104, 105 and 106, where tissues 103 and 104 corresponds to muscular tissue with different quality levels, associated to weights of 1 and 2 respectively; and tissues 105 and 106 corresponds to adipocytes and to calcified structure, associated to weights 0.5 and 0 respectively.

Said thickness function value associated to trajectory 109 is computed from a value of the arclength of said trajectory weighted with coefficients depending on classes assigned to the points of the mapping of points through with said trajectory encompasses. The thickness function value associated to trajectory 109 is computed by instantiating said arclength function value to 0, with traversing every point encompassed by said trajectory and with recursively computing a new value of said arclength value for each new traversed point, said new value being computed from previous value of said thickness function value and from the class assigned to said new traversed point.

In this embodiment, said new value is computed from the previous value of said thickness function value incremented by a factor whose value depends on the class assigned to said new traversed point.

Reference is made to FIG. 4C which shows a plot of the progression at each step of the computation of the thickness function value associated to trajectory 109 joining one point 108 of the inner border 102 to one point 107 of the outer border 101 and passing through points that have been classified into different classes during classification step 2.

In a subsequent step 5 of generation of a 3D model 1000 of said tissue from said mapping of points 10, at least to each voxel of said 3D model 1000 corresponding to the inner border 102 and/or to the outer border 101 of said tissue is assigned an adjusted thickness value determined from the value of the thickness function associated to the trajectory 109 encompassing said voxels and computed at step 4.

Reference is made to FIG. 5 which shows a 3D model returned by the method. In this embodiment, each voxel corresponding to the outer border of said tissue is assigned to a color determined from the adjusted thickness value assign to this voxel and associated to the arclength of the trajectory 19 passing through said voxel.

Each voxel of the 3D model is classified by its associated thickness function value determined previously according to a thickness range among the following thickness intervals: from 0 mm to 1 mm, from 1 mm to 2 mm, from 2 mm to 3 mm, from 3 mm to 4 mm, from 4 mm to 5 mm and larger than 5 mm.

In this way, the set of voxels belonging to the same thickness interval allows to define a mesh containing said set of voxels. By considering such a sub-mesh for each thickness interval it is possible to establish a partition of the 3D model by meshes whose points belong to the same thickness range.

The methods disclosed herein may also be implemented by software programs executable by a computer system. Further, implementations may include distributed processing and parallel processing, especially for processing in parallel several or all data in the data sets.

The illustrations described herein are intended to provide a general understanding of the structure of various embodiments. These illustrations are not intended to serve as a complete description of all the elements and features of apparatus, processors and systems that utilizes the structures or methods described therein. Many other embodiments or combinations thereof may be apparent to those of ordinary skills in the art upon reviewing the disclosure by combining the disclosed embodiments. Other embodiments may be utilized and derived from the disclosure, such that structural and logical substitutions and changes may be made without departing from the scope of the disclosure.

Further, the disclosure and the illustrations are to be considered as illustrative rather than restrictive, and the appended claims are intended to cover all such modifications, enhancements, and other embodiments, which fall within the true spirit and scope of the description. Thus, the scope of the following claims is to be determined by the broadest permissible interpretation of the claims and their equivalents and shall not be restricted or limited by the foregoing description.

We claim:

1. A computer-implemented method for the evaluation of an adjusted thickness of a tissue of an organ, the method comprising:

a. step (1) of receiving at least one mapping of points (10) representing said tissue, said mapping of points (10) defining an inner border (102) and an outer border (101) of said tissue;

b. step (2) of segmentation of the mapping of points (10) by classification of each point (11) from the mapping of points (10) into a class belonging to a set of different classes;

c. step (3) of determining a plurality of trajectories each joining one point (108) of the inner border (102) to one point (107) of the outer border (101);

d. step (4) of computing for each trajectory (109) the value of a thickness function, wherein said thickness function depends on said trajectory (109) and the classes assigned to the points of the mapping of points (10) through which said trajectory (109) encompasses, wherein the thickness function value is computed from a value of arclength of said trajectory (109) weighted with coefficients depending on the classes by instantiating the arclength function value to 0 and traversing a set of points of the mapping of points by recursively computing a new value of said arclength value for each new traversed point, said new value being computed from the previous value of said thickness function value and from the class assigned to said new traversed point; and e. step (5) of generation of a 3D model (1000) of said tissue from said mapping of points (10), wherein at least to one voxel of said 3D model (1000) is assigned an adjusted thickness value determined from the value of the thickness function associated to the trajectory (109) encompassing said voxel.

2. The method according to claim 1, wherein to each point (11) of the mapping of points (10) which is received is associated at least one value depending on the type of the tissue at a location corresponding to said point (11), and wherein the step (2) of segmentation is implemented by associating a class selected from the set of classes from said value associated to said point (11) of the mapping of points (10).

3. The method according to claim 1, wherein the segmentation classes comprise at least one class among muscle tissue (103,104), fat tissue (105) or calcified tissue (106).

4. The method according to claim 1, wherein the plurality of trajectories is defined from a vector field (110) pointing from the inner border (102) to the outer border (101).

5. The method according to claim 1, wherein said new value is computed from the previous value of said thickness function value incremented by a factor whose value depends on the class assigned to said new traversed point.

6. The method according to claim 5, wherein said factor value is a non-null step value when the class assigned to said new traversed point is a predetermined class and 0 otherwise.

7. The method according to claim 5, wherein said factor value depends on the number of points to which said predetermined class is assigned among a set of points included into a bounding region centered on said new traversed point.

8. The method according to claim 1, wherein to at least to each voxel of said 3D model (1000) corresponding to the inner border (102) and/or to the outer border (101) of said tissue is assigned an adjusted thickness value determined from the value of the thickness function associated to the trajectory (109) encompassing said voxels.

9. The method according to claim 8, wherein to each voxel of said 3D model (1000) corresponding to the inner border (102) and/or to the outer border (101) of said tissue is assigned a color determined from the adjusted thickness value assigned to this voxel, said color being selected from a set of colors each associated to a thickness range.

10. The method according to claim 1, wherein said generated 3D model (1000) of said tissue comprises a plurality of sub-meshes, and wherein each sub-mesh is associated to a predetermined thickness range and comprises each voxel of said 3D model whose adjusted thickness value assigned to this voxel belongs to this predetermined thickness range.

* * * * *